United States Patent
Kubota et al.

(10) Patent No.: US 11,744,550 B2
(45) Date of Patent: Sep. 5, 2023

(54) ULTRASOUND PROBE, ACOUSTIC LENS, ULTRASOUND DIAGNOSIS APPARATUS, AND COUPLER FOR ULTRASOUND PROBES

(71) Applicant: CANON MEDICAL SYSTEMS CORPORATION, Otawara (JP)

(72) Inventors: Reiko Kubota, Ota-ku (JP); Yoji Teramoto, Ota-ku (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 67 days.

(21) Appl. No.: 17/199,852

(22) Filed: Mar. 12, 2021

(65) Prior Publication Data
US 2021/0321984 A1 Oct. 21, 2021

(30) Foreign Application Priority Data
Mar. 12, 2020 (JP) ................. 2020-042691

(51) Int. Cl.
*A61B 8/00* (2006.01)
*G10K 11/30* (2006.01)

(52) U.S. Cl.
CPC .......... *A61B 8/4444* (2013.01); *A61B 8/4272* (2013.01); *A61B 8/4281* (2013.01); *G10K 11/30* (2013.01)

(58) Field of Classification Search
None
See application file for complete search history.

(56) References Cited

U.S. PATENT DOCUMENTS

2016/0297972 A1* 10/2016 Mori .................... C09D 201/00
2019/0015071 A1* 1/2019 Fujii ..................... A61B 8/4272

FOREIGN PATENT DOCUMENTS

| JP | 2008-209257 A | 9/2008 |
| JP | 2019-17637 A | 7/2019 |
| WO | WO 2014/129649 A1 | 8/2014 |
| WO | WO 2015/098741 A1 | 7/2015 |

* cited by examiner

*Primary Examiner* — Colin T. Sakamoto
*Assistant Examiner* — Marjan Saboktakin
(74) *Attorney, Agent, or Firm* — Oblon, McClelland, Maier & Neustadt, L.L.P.

(57) ABSTRACT

An ultrasound probe according to an embodiment includes a base material, a first organic layer, and a second organic layer. The base material contain polyolefin. The first organic layer is formed on the outer surface of the base material and contains epoxy resin and silicate oligomer. The second organic layer is formed on the outer surface of the first organic layer and has hydrophilicity.

9 Claims, 4 Drawing Sheets

REFLECTION

(BEFORE FITTING)

(FITTING)

(AFTER FITTING)

ULTRASOUND PROBE, ACOUSTIC LENS, ULTRASOUND DIAGNOSIS APPARATUS, AND COUPLER FOR ULTRASOUND PROBES

CROSS-REFERENCE TO RELATED APPLICATIONS

This application is based upon and claims the benefit of priority from Japanese Patent Application No. 2020-042691, filed on Mar. 12, 2020; the entire contents of which are incorporated herein by reference.

FIELD

An embodiment disclosed in the present written description and the drawings is related to an ultrasound probe, an acoustic lens, an ultrasound diagnosis apparatus, and a coupler for ultrasound probes.

BACKGROUND

Conventionally, in an ultrasound diagnosis apparatus, an ultrasound probe is used that transmits and receives ultrasound when abutted against the body surface of the subject. In the leading end portion of the ultrasound probe, that is, in the portion that gets abutted against the body surface of the subject; an acoustic lens is installed for transmitting/focusing the ultrasound with efficiency. At the time of performing ultrasound imaging, the acoustic lens is disinfected using a disinfectant and a gel is applied thereto before abutting it against the body surface of the subject.

In view of its role, the acoustic lens is required to have a small attenuation coefficient for ultrasound, to have affinity (hydrophilicity) with gels, and to have high resistance to disinfectants. However, it is not easy to have an acoustic lens with all those features, and various technologies have been proposed to equip an acoustic lens with those features.

DETAILED DESCRIPTION

An ultrasound probe according to an embodiment includes a base material, a first organic layer, and a second organic layer. The base material contains polyolefin. The first organic layer is formed on the outer surface of the base material, and contains epoxy resin and silicate oligomer. The second organic layer is formed on the outer surface of the first organic layer, and has hydrophilicity.

The embodiment of the ultrasound probe, an acoustic lens, an ultrasound diagnosis apparatus, and a coupler for ultrasound probes is described below with reference to the accompanying drawings. However, the embodiment described below is not the only possible embodiment. Moreover, as a matter of principle, the details explained in one embodiment are identically applicable in another embodiment.

Embodiment

Figure 1:
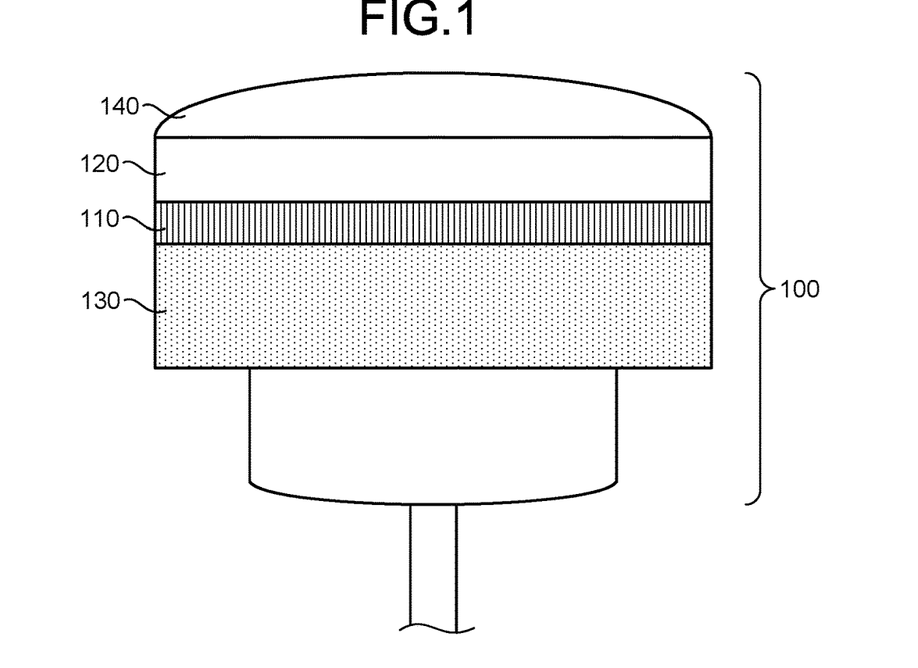
FIG. 1 is a diagram illustrating an exemplary configuration of an ultrasound probe according to an embodiment.

Explained below with reference to FIG. 1 is an exemplary configuration of an ultrasound probe 100 according to the embodiment. FIG. 1 is a diagram illustrating an exemplary configuration of the ultrasound probe 100 according to the embodiment. As illustrated in FIG. 1, for example, the ultrasound probe 100 according to the embodiment transmits ultrasound to the subject; receives ultrasound (reflected waves) that are reflected from the inside of the subject; converts the reflected waves into received signals; and transmits the received signals to an ultrasound diagnosis apparatus (the main body). For example, the ultrasound probe 100 includes a transducer array 110, a matching layer 120, a backing layer 130, and an acoustic lens 140.

The transducer array 110 includes a plurality of oscillators (piezoelectric transducer), and generates ultrasound based on the drive signals supplied from the ultrasound diagnosis apparatus. Moreover, the transducer array 110 receives ultrasound (reflected waves) reflected from the inside of the subject, and converts them into received signals.

As far as the arrangement of the transducer array 110 is concerned, any known arrangement method can be arbitrarily implemented. For example, the transducer array 110 either can be a 1D array probe in which a plurality of oscillators is arranged in a one-dimensional manner, or can be a 2D array probe in which a plurality of oscillators is arranged in a two-dimensional manner. Examples of a 1D array probe include a phased array probe, a linear array probe, and a convex array probe. Alternatively, the transducer array 110 can be a mechanical 4D array probe in which the ultrasound scan is performed while making a plurality of oscillators, which is arranged in line, oscillate at a predetermined angle (swinging angle).

The matching layer 120 is an intermediate substance that is meant for efficiently propagating the ultrasound inside the subject and that matches the oscillators with the acoustic impedance of the subject.

The backing layer 130 is a member that attenuates the ultrasound propagating backward from the transducer array 110 (i.e., propagating in the opposite direction to the direction of transmission of ultrasound).

The acoustic lens 140 is a lens for focusing the ultrasound. For example, the acoustic lens 140 is bonded with the matching layer 120 via an arbitrary bonding adhesive. Moreover, the acoustic lens 140 has a shape that enables focusing of ultrasound. For example, the outer surface of the acoustic lens 140 has a convex surface with a raised central portion.

Meanwhile, as long as focusing of the ultrasound is possible, the acoustic lens 140 is not limited to have a convex surface, and can alternatively have a planar surface or a concave surface. Moreover, the acoustic lens 140 can be prepared of two or more layers. Furthermore, the outer surface of the acoustic lens 140 can have asperity or can be flat, although it is desirable that an arithmetic mean roughness Ra is equal to or smaller than 5 μm.

Figure 2:
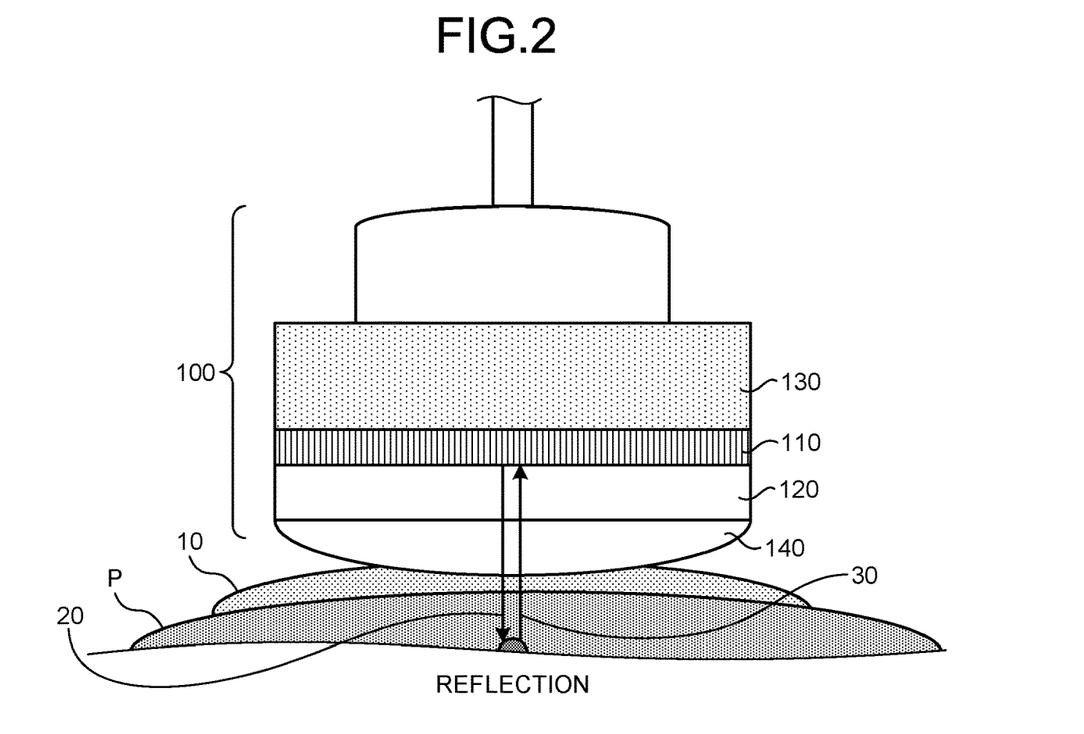
FIG. 2 is a diagram for explaining about the ultrasound scan performed by the ultrasound probe according to the embodiment.

Explained below with reference to FIG. 2 is the ultrasound scan performed by the ultrasound probe 100. FIG. 2 is a diagram for explaining about the ultrasound scan performed by the ultrasound probe 100 according to the embodiment.

As illustrated in FIG. 2, the ultrasound probe 100 is abutted against the body surface of a subject P, with a gel 10 applied to the outer surface of the acoustic lens 140.

Then, the ultrasound probe 100 transmits an ultrasound 20 from the transducer array 110 to the inside of the body of the subject P. The ultrasound 20, which is transmitted to the inside of the body of the subject P, gets reflected from the discontinuous surface of acoustic impedance and is received as a reflected wave 30 by the transducer array 110. The signal of the received reflected wave 30 is then transmitted as a received signal to the ultrasound diagnosis apparatus. Based on the received signal, the ultrasound diagnosis apparatus generates an ultrasound image such as a B-mode image or a doppler image.

Meanwhile, in recent years, in order to generate high-definition ultrasound images, achieving sophistication of ultrasound probes is being studied. In order to generate high-definition ultrasound images, it is possible to think of increasing the frequency of the ultrasound that are transmitted. However, increasing the frequency leads to having a greater impact of the attenuation coefficient attributed to the material. Hence, in order to hold down the attenuation of the ultrasound generated from a transducer array; it is desirable that a material having a small attenuation coefficient is selected as the base material of the acoustic lens. Moreover, in order to clean the gel and the dust attached thereto or to disinfect it, the outer surface of the acoustic lens is often wiped with a paper or a piece of cloth that is moistened with a disinfectant. Hence, the outer surface of the acoustic lens is required to have high resistance (water resistance).

As a material that satisfies the attenuation coefficient and the resistance mentioned above, it is possible to consider polyolefin. However, since polyolefin is hydrophobic in nature, it has low affinity (low hydrophilicity) with gels. If there is low affinity (low hydrophilicity) with gels, air bubbles develop on the outer surface of the acoustic lens during an ultrasound scan, which may affect the image quality of the ultrasound images.

In that regard, as a result of having the configuration explained below, the ultrasound probe 100 according to the embodiment enables achieving reduction of the attenuation coefficient in the acoustic lens and achieving enhancement in hydrophilicity and resistance (abrasion resistance) therein. That is, in the ultrasound probe 100, the acoustic lens 140 includes a base material that contains polyolefin; a first organic layer that contains epoxy resin and silicate oligomer; and a second organic layer that is formed on the outer surface of the first organic layer and that has hydrophilicity.

Figure 3:
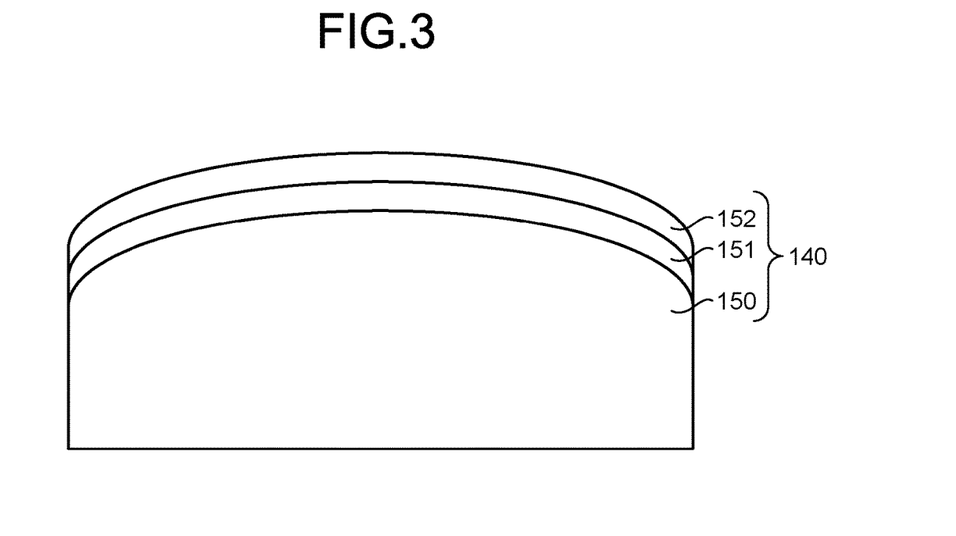
FIG. 3 is a diagram illustrating an exemplary configuration of an acoustic lens according to the embodiment.

Explained below with reference to FIG. 3 is an exemplary configuration of the acoustic lens 140 according to the embodiment. FIG. 3 is a diagram illustrating an exemplary configuration of the acoustic lens 140 according to the embodiment. In FIG. 3 is illustrated a cross-sectional view of the acoustic lens 140.

As illustrated in FIG. 3, for example, the acoustic lens 140 includes a base material 150, an organic layer 151, and an organic layer 152. With reference to FIG. 3, the base material 150 is a portion that is bonded to the matching layer 120; and the organic layer 152 is a portion that gets abutted against the body surface of the subject P. Herein, the organic layer 151 represents an example of the first organic layer, and the organic layer 152 represents an example of the second organic layer.

(Configuration of base material 150)

The base material 150 contains polyolefin. From the perspective of obtaining excellent ultrasound images, it is desirable that the quality of material of the base material 150 has a small attenuation coefficient and has the acoustic impedance close to the water present in the gel 10. As far as the type of polyolefin is concerned, a known material can be arbitrarily selected. Examples of polyolefin include polypropylene, polyethylene, and polymethyl pentene; and it is more desirable to use polymethyl pentene from the perspective of acoustic characteristics. The polyolefin can contain a chromatic material such as titanium oxide or carbon black, along with containing some other minor components.

(Method for Manufacturing Base Material 150)

The base material 150 can be manufactured according to an arbitrary manufacturing method. As an example, the base material 150 can be manufactured according to injection molding, transfer molding, casting, compression molding, cutting machining, or 3D printing.

(Configuration of organic layer 151)

The organic layer 151 is formed on the outer surface of the base material 150, and contains epoxy resin and silicate oligomer.

The epoxy resin included in the organic layer 151 can be an arbitrary type of epoxy resin. Examples of the epoxy resin include bisphenol A, bisphenol F, glycidyl ester epoxy resin, biphenyl epoxy resin, phenoxy epoxy resin, and polyfunctional epoxy resin. Herein, in the organic layer 151, either only one type of epoxy resin can be used, or a mixture of a plurality of types of epoxy resin can be used.

The silicate oligomer included in the organic layer 151 can be an arbitrary type of silicate oligomer. Examples of the silicate oligomer include methyl silicate oligomer and ethyl silicate oligomer. Herein, in the organic layer 151, either only one type of silicate oligomer can be used, or a mixture of a plurality of types of silicate oligomer can be used. That is, in the organic layer 151, at least either the methyl silicate oligomer or the ethyl silicate oligomer is included as the silicate oligomer.

Meanwhile, the organic layer 151 can also contain other components in the coating material, such as a curing agent, a UV initiator, a solvent medium, a diluent, a plasticizer, a coupling agent, an antimicrobial agent, an antiseptic agent, inorganic matter, and a dye. Regarding the curing agent, an arbitrary agent can be used as long as epoxy resin can be cured. Examples of the curing agent include the amine series, the mercaptan series, the ketimine series, the imidazole series, the acid anhydride series, the phenol series, the dicyandiamide series, and an UV initiator. Herein, either only one of those curing agents can be used, or a mixture of a plurality of curing agents can be used. Regarding the solvent medium, an arbitrary medium can be used as long as epoxy resin and silicate oligomer can dissolve. Examples of the solvent medium include propylene glycol monomethyl ether, propylene glycol monobutyl ether, propylene glycol monomethyl ether acetate, methyl ethyl ketone, methyl isobutyl ketone, xylene, toluene, benzyl alcohol, isopropyl alcohol, acetone, and ethanol. Herein, either only one of those organic solvents can be used, or a mixture of a plurality of organic solvents can be used.

(Method for manufacturing organic layer 151)

Given below is the explanation about the method for manufacturing the organic layer 151. Firstly, in order to form the organic layer 151, a coating material including at least epoxy resin and silicate oligomer is prepared; a film of the prepared coating material is formed on the outer surface of the base material 150; and the film is cured. The following explanation is given about the method for preparing the coating material for the organic layer 151, the film formation method, and the curing method.

Firstly, the explanation is given about the method for preparing the coating material for the organic layer 151. In the coating material for the organic layer 151, at least epoxy resin and silicate oligomer are used. Moreover, a curing agent and a solvent medium can be included as other components; and all materials are used in mixture. Regarding epoxy resin, it is desirable that the content is equal to or greater than 30 weight percent and equal to or smaller than 99 weight percent. If the content of epoxy resin is smaller than 30 weight percent, then it may result in a decline in the adhesiveness of the film. On the other hand, if the content of epoxy resin is greater than 99 weight percent, then the coating properties may deteriorate. Regarding silicate oligomer, it is desirable that the content is equal to or greater than 0.1 weight percent and equal to or smaller than 35 weight percent. If the content of silicate oligomer is smaller than 0.1 weight percent, then the coating properties may deteriorate. On the other hand, if the content of silicon oligomer is greater than 35 weight percent, then the adhesiveness may deteriorate.

The following explanation is given about the method for forming a film of the coating material on the organic layer 151. As long as the desired film thickness can be achieved, an arbitrary method can be implemented to form a film of the coating material on the organic layer 151. Examples of the film formation method include spin coating, dip coating, bar coating, transfer printing, spray coating, and electrostatic coating. As far as the coating range is concerned, either the film can be formed across the entire surface or the film can be formed only in the portion through which ultrasound pass.

The film thickness of the organic layer 151 is desirably equal to or greater than 3 μm and equal to or smaller than 20 μm, and is more desirably equal to or greater than 5 μm and equal to or smaller than 15 μm. If the film thickness of the organic layer 151 is smaller than 3 μm, then the abrasion resistance may deteriorate. On the other hand, if the film thickness of the organic layer 151 is greater than 20 μm, then the acoustic characteristics may deteriorate.

The following explanation is given about the method for curing the organic layer 151. The coating material on the organic layer 151 can be cured according to an arbitrary method. Examples of the curing method include thermal curing, UV curing, and cold drying.

Moreover, the organic layer 151 can be subjected to surface treatment for the purpose of enhancing the adhesiveness with respect to the base material 150. Examples of surface treatment include UV ozone treatment, plasma treatment, corona discharge, and Itro treatment. Herein, either only one type of surface treatment can be performed, or a plurality of types of surface treatment can be performed.

Meanwhile, after the organic layer 151 is manufactured, when water enters the organic layer 151, silicate oligomer included in the organic layer 151 reacts with water (undergoes hydrolysis) due to which a film of silicon oxide (silicon dioxide) gets formed. That is, the organic layer 151 contains silicon oxide as a result of hydrolysis of silicate oligomer.

(Mixing ratio of materials in organic layer 151)

Regarding the ratio of the materials included during film coating on the organic layer 151, it is desirable that the content ratio of epoxy resin and silicate oligomer is in the range of 10:0.1 volume percent to 10:5 volume percent. Moreover, it is more desirable that the content ratio of epoxy resin and silicate oligomer is in the range of 10:1 volume percent to 10:2 volume percent. If the content ratio of epoxy resin and silicate oligomer is smaller than 10:0.1 volume percent, then the coating properties with respect to the base material 150 may deteriorate. On the other hand, if the content ratio of epoxy resin and silicate oligomer is greater than 10:5 volume percent, then the water resistance may deteriorate.

(Configuration of Organic Layer 152)

The organic layer 152 is formed on the outer surface of the organic layer 151, and has hydrophilicity. Herein, as long as hydrophilicity is achieved, the organic layer 152 can be prepared of any arbitrary material. Examples of a hydrophilic material include acrylate, urethane, urethane acrylate, silicon, silsesquioxane, phenol, and an organic-inorganic hybrid system. Herein, either only one hydrophilic material can be used, or a mixture of a plurality of hydrophilic materials can be used.

Meanwhile, the organic layer 152 desirably has the water contact angle equal to or smaller than 70°, and more desirably has the water contact angle equal to or smaller than 60°. If the water contact angle is greater than 70°, then the gel 10 is likely to develop air bubbles, which may deteriorate the image quality of ultrasound images. Meanwhile, the organic layer 152 desirably has the film hardness equal to or greater than 2H in terms of pencil hardness, and more desirably has the film hardness equal to or greater than 3H. If the pencil hardness is smaller than 2H, then the abrasion resistance at the time of performing gel contact evaluation may deteriorate, and the hydrophilic film may come off due to scraping.

Subsequently, a curing agent, a UV initiator, a solvent medium, a diluent, a plasticizer, a coupling agent, an antimicrobial agent, an antiseptic agent, inorganic matter, and a dye can be added in the coating material as other components. Regarding the curing agent, an arbitrary agent can be used as long as the organic layer 152 can be cured. Examples of the curing agent include a thermal curing agent and a UV initiator. Herein, only one curing agent can be used, or a mixture of a plurality of curing agents can be used. Regarding the solvent medium, an arbitrary medium can be used as long as the organic layer 152 can dissolve. Examples of the solvent medium (organic solvent) include propylene glycol monomethyl ether, propylene glycol monobutyl ether, propylene glycol monomethyl ether acetate, methyl ethyl ketone, methyl isobutyl ketone, xylene, toluene, benzyl alcohol, isopropyl alcohol, acetone, and ethanol. Herein, either only one of those organic solvents can be used, or a mixture of a plurality of organic solvents can be used.

(Method for Manufacturing Organic Layer 152)

Given below is the explanation about the method for manufacturing the organic layer 152. Firstly, in order to form the organic layer 152, a coating material is prepared; a film of the prepared coating material is formed on the outer surface of the organic layer 151; and the film is cured. The following explanation is given about the method for preparing the coating material for the organic layer 152, the film formation method, and the curing method.

Firstly, the explanation is given about the method for preparing the coating material for the organic layer 152. In the coating material for the organic layer 152 according to the present invention, a material at least having hydrophilicity is used. Moreover, a curing agent and a solvent medium can be included as other components; and all materials are used in mixture.

The following explanation is given about the method for forming a film of the coating material on the organic layer 152. As long as the desired film thickness can be achieved, an arbitrary method can be implemented to form a film of the coating material on the organic layer 152. Examples of the film formation method include spin coating, dip coating, bar coating, transfer printing, spray coating, and electrostatic coating. As far as the coating range is concerned, it is desirable that the film is formed across the entire top surface of the organic layer 151. However, the film need not be formed across the entire top surface of the organic layer 151. Alternatively, for example, as long as the film can be formed on the surface that gets abutted with the body surface of the subject P, it serves the purpose.

The film thickness of the organic layer 152 is desirably equal to or greater than 3 μm and equal to or smaller than 20 μm, and is more desirably equal to or greater than 4 μm and equal to or smaller than 15 μm. If the film thickness of the organic layer 152 is smaller than 3 μm, then the film may get completely scraped due to the abrasion at the time of evaluation. On the other hand, if the film thickness of the organic layer 152 is greater than 20 μm, then the acoustic characteristics may deteriorate.

The following explanation is given about the method for curing the organic layer 152. The coating material on the organic layer 152 can be cured according to an arbitrary method. Examples of the curing method include thermal curing, UV curing, and cold drying.

Moreover, the organic layer 152 can be subjected to surface treatment for the purpose of enhancing the adhesiveness with respect to the organic layer 151. Examples of the surface treatment include UV ozone treatment, plasma treatment, corona discharge, and Itro treatment. Herein, either only one type of surface treatment can be performed, or a plurality of types of surface treatment can be performed.

(Gel)

Regarding the gel 10 used in the ultrasound probe 100, it is possible to arbitrarily apply a known gel. For example, any arbitrary gel that is commonly used in ultrasound diagnosis apparatuses can be applied.

Meanwhile, the details explained with reference to FIGS. 1 to 3 are only exemplary, and the embodiment is not limited by those details. For example, in regard to the transducer array 110, the matching layer 120, the backing layer 130, and the gel 10; any known technologies can be implemented.

(Characteristics of Acoustic Lens 140)

Figure 4:
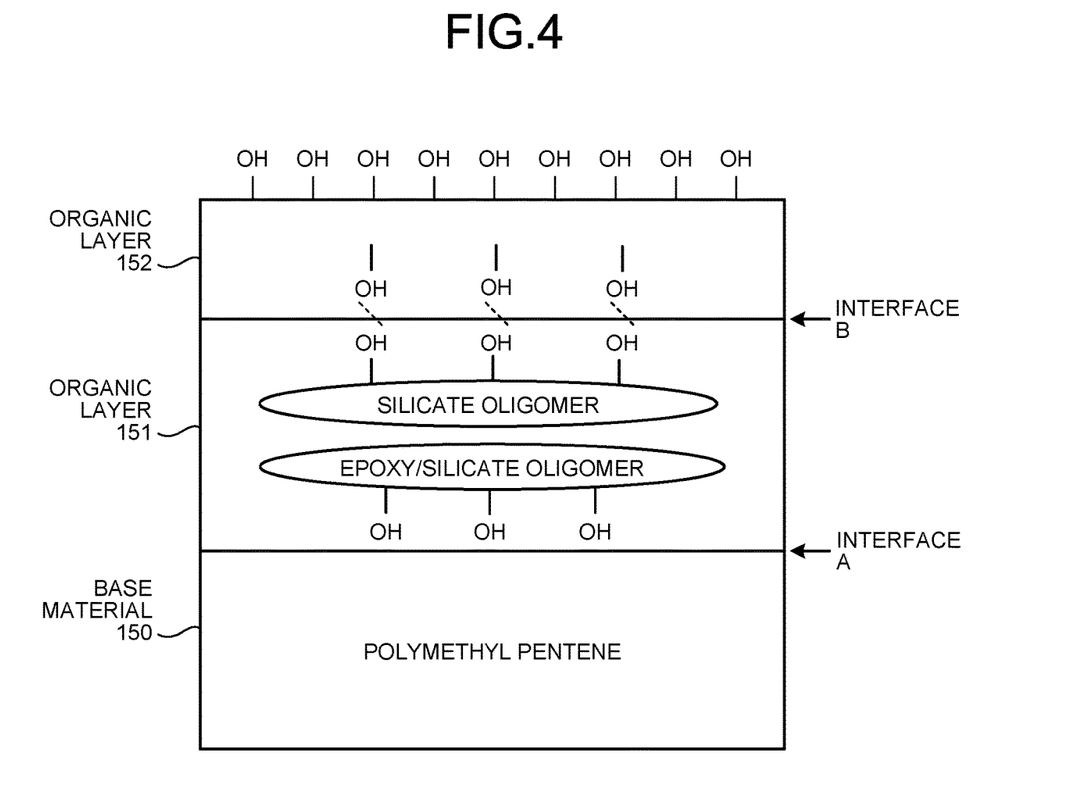
FIG. 4 is a diagram for explaining the characteristics of the acoustic lens according to the embodiment.

Explained below with FIG. 4 are the characteristics of the acoustic lens 140 according to the embodiment. FIG. 4 is a diagram for explaining the characteristics of the acoustic lens 140 according to the embodiment. In FIG. 4, an interface A represents the surface between the base material 150 and the organic layer 151, and an interface B represents the surface between the organic layers 151 and 152.

As illustrated in FIG. 4, in the ultrasound probe 100, the acoustic lens 140 includes the base material 150 that contains polyolefin. As a result, the acoustic lens 140 enables achieving reduction in the attenuation coefficient and achieving enhancement in water resistance.

Moreover, in the ultrasound probe 100 according to the embodiment, the acoustic lens 140 includes the hydrophilic organic layer 152 as the outermost layer (i.e., the surface that gets abutted against the body surface of the subject P). Because of its hydrophilicity, the organic layer 152 holds down the development of air bubbles in between the surface of the acoustic lens 140 and the gel 10.

However, because of the high water penetrability of the organic layer 152, the deterioration in the adhesiveness with respect to the base material 150 (polyolefin) is a matter of concern. In that regard, in the present embodiment, on the outer surface of the base material 150, the organic layer 151 is coated as a primer. The organic layer 151 contains silicate oligomer. Thus, at the interface B, the silicate oligomer of the organic layer 151 reacts with water that has entered, and turns into a strong film of silicon oxide (silicon dioxide). Hence, the adhesiveness does not deteriorate. Moreover, since the reaction leads to the expression of the hydroxyl group (OH group), hydrogen bonding occurs between the silicate oligomer and the hydrophilic group of the organic layer 152. Accordingly, it is presumed that the adhesiveness is further enhanced.

Meanwhile, since polyolefin has a low degree of adhesiveness, even if the film of a commonly-used resin is formed as the primer, the coating properties are poor and the adhesiveness deteriorates by further entry of water. In that regard, the organic layer 151 according to the embodiment contains epoxy resin and silicate oligomer. Hence, the organic layer 151 has a significantly high degree of affinity with polyolefin, thereby enabling achieving excellent adhesiveness and excellent water resistance.

With such characteristics, the ultrasound probe 100 enables achieving reduction of the attenuation coefficient in the acoustic lens 140 and achieving enhancement in hydrophilicity and resistance (abrasion resistance) therein.

Meanwhile, the embodiment is not limited by the explanation given above. That is, configurations having appropriate combinations of the abovementioned constituent elements are also included in the present invention. Moreover, further effects and modification examples can be easily derived by a person skilled in the art. Hence, the aspects of the embodiment having a wider scope are not limited to the embodiment described above, and can be modified in a variety of ways.

(Application in Ultrasound Diagnosis Apparatus)

The present embodiment can also be provided in the form of an ultrasound diagnosis apparatus.

Figure 5:
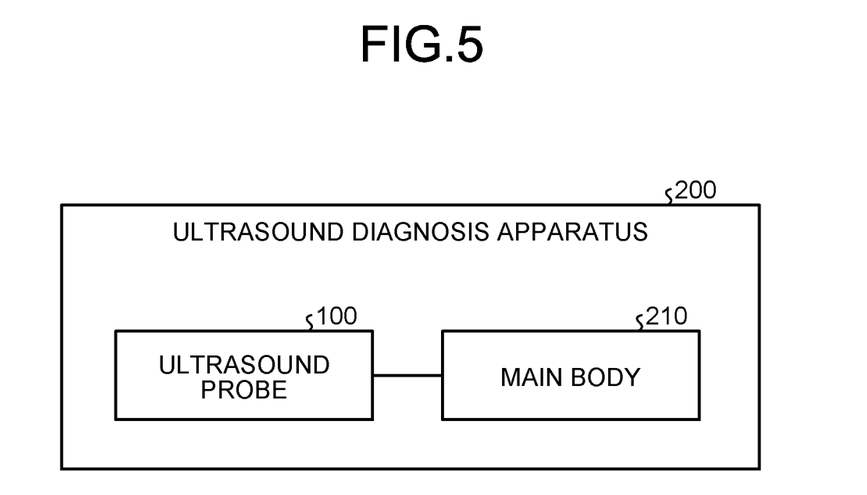
FIG. 5 is a diagram illustrating an exemplary configuration of an ultrasound diagnosis apparatus according to the embodiment.

Explained below with reference to FIG. 5 is an exemplary configuration of an ultrasound diagnosis apparatus 200 according to the embodiment. FIG. 5 is a diagram illustrating an exemplary configuration of the ultrasound diagnosis apparatus 200 according to the embodiment. As illustrated in FIG. 5, the ultrasound diagnosis apparatus 200 includes the ultrasound probe 100 according to the embodiment and includes a main body 210. Herein, the configuration of the ultrasound probe 100 is identical to the configuration thereof according to the embodiment described above. Hence, that explanation is not given again.

The main body 210 generates, for example, ultrasound images based on the received signals collected by the ultrasound probe 100, and displays the generated ultrasound images. The main body 210 can have the configuration based on any arbitrary known technology. Hence, that explanation is not given.

(Application in Sophisticated Ultrasound Probe)

In recent years, a technology has been known in which the major functions related to the transmission and reception of ultrasound are incorporated in the housing of an ultrasound probe, and an ultrasound diagnosis apparatus is configured by connecting the ultrasound probe (hereinafter, called a "sophisticated ultrasound probe") to a general-purpose information processing device such as a personal computer or a tablet terminal. The ultrasound probe 100 according to the embodiment described above can be implemented as a sophisticated ultrasound probe.

(Application in Acoustic Coupler)

The present embodiment can also be provided as an acoustic coupler. An acoustic coupler is an instrument attached to the acoustic radiation surface of an ultrasound probe. For example, an acoustic coupler is attached to the acoustic radiation surface of an ultrasound probe with the aim of varying the sound focus position and expanding the contact area with the subject. An acoustic coupler represents an example of a coupler for ultrasound probes.

Figure 6:
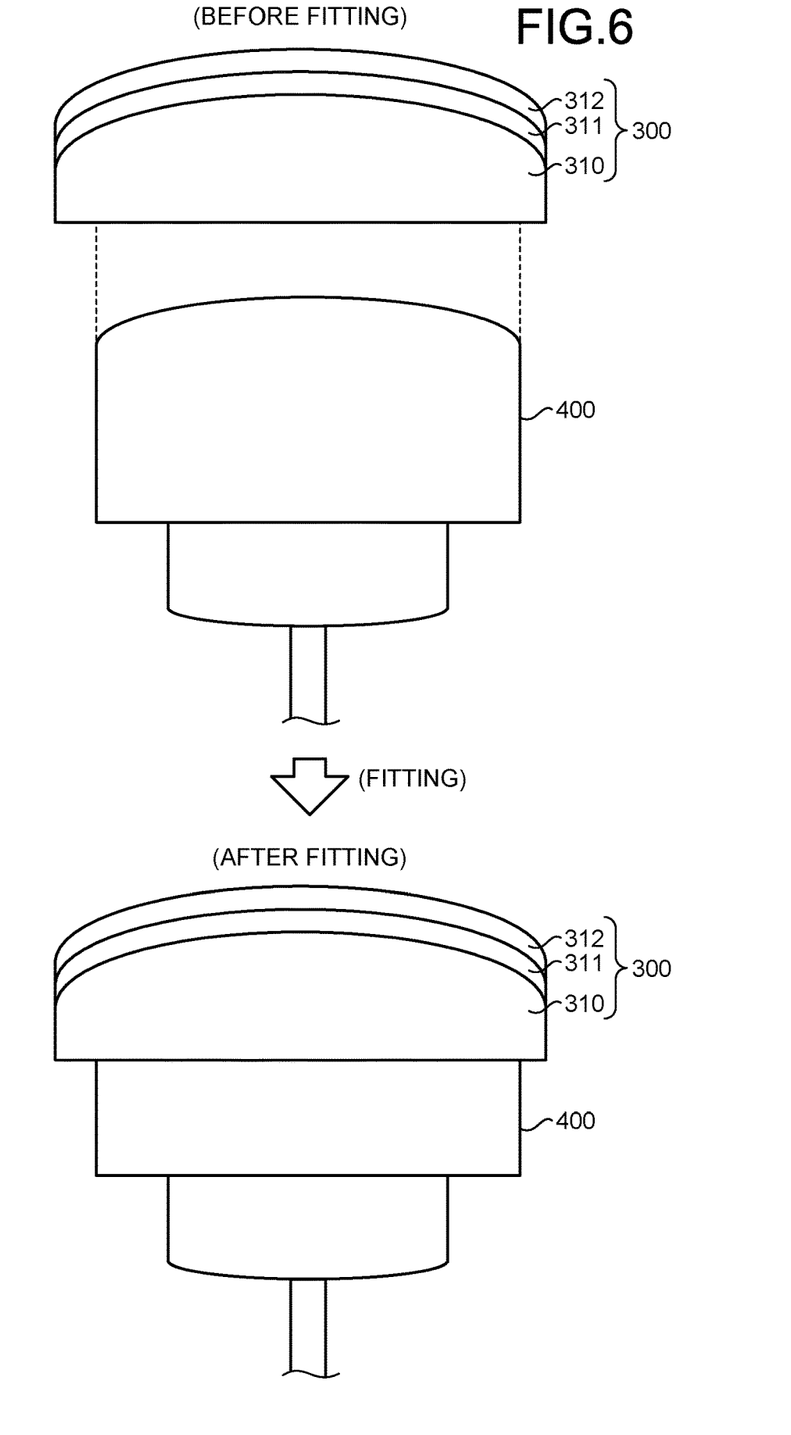
FIG. 6 is a diagram illustrating an exemplary configuration of an acoustic coupler according to the embodiment.

Explained with reference to FIG. 6 is an exemplary configuration of an acoustic coupler according to the embodiment. FIG. 6 is a diagram illustrating an exemplary configuration of an acoustic coupler according to the embodiment. In FIG. 6 is illustrated the transition from the state in which an acoustic coupler 300 is not yet fit onto the acoustic radiation surface of an ultrasound probe 400 to the state in which the acoustic coupler 300 has been fit.

As illustrated in FIG. 6, the acoustic coupler is attached in a detachably-attachable manner to the acoustic radiation surface of the ultrasound probe 400. At that time, the acoustic coupler 300 and the ultrasound probe 400 are interlocked along the dashed lines illustrated in FIG. 6, and are configured to fit with each other. Meanwhile, in the ultrasound probe 400, either any known acoustic lens can be arbitrarily used, or the acoustic lens 140 explained earlier can be used.

The acoustic coupler 300 includes a base material 310, an organic layer 311, and an organic layer 312. The base material 310 has an identical configuration to the configuration of the base material 150 illustrated in FIG. 3, and is manufactured according to an identical method to the method for manufacturing the base material 150. The organic layer 311 has an identical configuration to the configuration of the organic layer 151 illustrated in FIG. 3, and is manufactured according to an identical method to the method for manufacturing the organic layer 151. The organic layer 312 has an identical configuration to the configuration of the organic layer 152 illustrated in FIG. 3, and is manufactured according to an identical method to the method for manufacturing the organic layer 152.

That is, the acoustic coupler 300 includes the base material 310 that contains olefin; includes the organic layer 311 that is formed on the outer surface of the base material 310 and that contains epoxy resin and silicate oligomer; and includes the organic layer 312 that is formed on the outer surface of the organic layer 311 and that has hydrophilicity. As a result, the acoustic coupler 300 enables achieving reduction in the attenuation coefficient and enables achieving enhancement in hydrophilicity and water resistance.

WORKING EXAMPLES

Given below is the explanation of preferred working examples. In a first working example to a 12-th working example; the adjustment of the coating material, the formation/curing of the film, the evaluation of water resistance, and the evaluation of hydrophilicity was performed in the following manner.

[Water Resistance]

The following explanation is given about the method for evaluating water resistance. Firstly, a measurement sample having the film according to the present invention formed therein was immersed in a glass container and the glass container was heated to 60° C. in a thermostatic oven; and, after 1300 hours, a measurement sample having the film according to the present embodiment (corresponding to the organic layers 151 and 152) formed therein was taken out. Subsequently, the measurement sample was subjected to the crosscut test (based on JIS 560-5-6) for evaluating the adhesiveness. Moreover, the external appearance was visually checked, and it was confirmed whether or not there are any changes such as whether the film has come off or has unstuck portions.

As the gel, SONO JELLY-M (Cannon Medical Systems) was used. As the thermostatic oven, OFW-3005 (AS ONE CORPORATION.) was used. As the measurement sample, a film of the organic layers 151 and 152 was formed on a polymethyl pentene board having the thickness of 5 mm at 30 mm angle.

After the water resistance test is performed, if there is no peeling off of the film surface and no change in the external appearance during the crosscut test, then the film can be said to be an exceptionally good film. On the other hand, after the water resistance test is performed, if there is peeling off of the film surface but no change in the external appearance during the crosscut test, then the film can be said to be a good film. Moreover, after the water resistance test is performed, if there is no peeling off of the film surface but some change in the external appearance during the crosscut test, then the film can be said to be a somewhat good film. However, after the water resistance test is performed, if there is peeling off of the film surface and some change in the external appearance during the crosscut test, then the film cannot be said to be a good film.

(Four-Stage Evaluation of Water Resistance)

A: there is no peeling off and no change in the external appearance during the crosscut test B: there is peeling off but no change in the external appearance during the crosscut test C: there is no peeling off in crosscut test but some change in the external appearance during the crosscut test D: there is peeling off and some change in the external appearance during the crosscut test

[Hydrophilicity]

The following explanation is given about the method for evaluating hydrophilicity. The hydrophilicity was evaluated by measuring the contact angle of water (pure water) using a contact angle meter (VCA-2500: Tech Science) in a measurement sample. As the measurement sample, a film of the organic layers 151 and 152 was formed on a polymethyl pentene board having the thickness of 5 mm at 30 mm angle.

As far as the hydrophilicity is concerned, the film can be said to be an exceptionally good film if the contact angle is smaller than 60°. Alternatively, the film can be said to be a good film if the contact angle is smaller than 70°. However, the film cannot be said to be a good film if the contact angle is equal to or greater than 70°.

(Three-Stage Evaluation of Hydrophilicity)

A: the contact angle is smaller than 60°

B: the contact angle is equal to or greater than 60° but smaller than 70°

C: the contact angle is equal to or greater than 70°

[Pencil Hardness]

The following explanation is given about the method for evaluating the pencil hardness. The pencil hardness was evaluated based on JIS 5600-5-4. As the measurement sample, a film of the organic layers 151 and 152 was formed on a polymethyl pentene board having the thickness of 5 mm at 30 mm angle.

The film can be said to be an exceptionally good film in the case of having the pencil hardness equal to or greater than 3H. Alternatively, the film can be said to be a good film in the case of having the pencil hardness equal to or greater than 2H but smaller than 3H.

[Evaluation of Ultrasound Images Based on Development or No Development of Air Bubbles in Gel]

The following explanation is given about the evaluation of ultrasound images based on the development or no development of air bubbles in the gel. An acoustic lens having the film according to the present embodiment formed therein was incorporated in an ultrasound probe; ultrasound images were taken by connecting the ultrasound probe to an ultrasound diagnosis apparatus; and the deterioration or no deterioration in the ultrasound images due to the development of air bubbles was evaluated.

On a biological object (a subject), the ultrasound probe was moved back and forth for a distance of 5 cm for five times at the speed of 5 cm per second, and an image was taken immediately after the movement. Then, the surface having bubbles had high luminance, and the amount of black dot defects in the portions in which the ultrasound did not reach (hereinafter, referred to as a black dot defect amount) was evaluated from the ultrasound image. The evaluation was performed for five times, and the average value was taken.

If the black dot defect amount in the ultrasound images is lower than 1%, then the film can be said to be an exceptionally good film. On the other hand, if the black dot defect amount in the ultrasound images is equal to or higher than 1% but lower than 10%, then the film can be said to be a good film. Moreover, if the black dot defect amount in the ultrasound image is equal to or higher than 10% but lower than 15%, then the film can be said to be a somewhat good film. However, if the black dot defect amount in the ultrasound image is equal to or higher 15%, then the film cannot be said to be a good film.

(Four-Stage Evaluation of Black Dot Defects in Ultrasound Images)

A: the black dot defect amount in ultrasound images is lower than 1%

B: the black dot defect amount in ultrasound images is equal to or higher than 1% but lower than 10%

C: the black dot defect amount in ultrasound images is equal to or higher than 10% but lower than 15%

D: the black dot defect amount in ultrasound images is equal to or higher than 15%

[Evaluation of Ultrasound Images During Inactivity of Ultrasound Probe]

The following explanation is given about the evaluation of ultrasound images during the inactivity of the ultrasound probe. An acoustic lens having the film according to the present embodiment formed therein was incorporated in an ultrasound probe; the ultrasound probe was connected to an ultrasound diagnosis apparatus; and ultrasound images were evaluated. Firstly, an ultrasound image was taken using an ultrasound probe not having the film according to the present embodiment formed therein; and then an ultrasound image was taken using an ultrasound probe having the film according to the present embodiment formed therein. Subsequently, the luminance of each ultrasound image was measured and, if the luminance for the ultrasound probe not having the film according to the present embodiment formed therein is considered 100%, the luminance ratio for the ultrasound probe having the film according to the present embodiment formed therein was calculated for distinguishing between the sharpness of those ultrasound images.

If the luminance ratio of the ultrasound images is equal to or higher than 95%, then the film can be said to be an exceptionally good film. On the other hand, if the luminance ratio of the ultrasound images is equal to or higher than 90% but lower than 95%, then the film can be said to be a good film. However, if the luminance ratio of the ultrasound images is lower than 90%, then the film cannot be said to be a good film.

(Three-Stage Evaluation of Ultrasound Images During Inactivity of Ultrasound Probe)

A: the luminance ratio of ultrasound images is equal to or higher than 95%

B: the luminance ratio of ultrasound images is equal to or higher than 90% but lower than 95%

C: the luminance ratio of ultrasound images is lower than 90%

First Working Example

<Adjustment of Coating Material>

In the first working example, the coating material was prepared in the following manner. Regarding the organic layer 151; 100 g of epoxy resin (coating film equivalent of 71.4 volume percent), 10 g of methyl silicate oligomer (coating film equivalent of 7.1 volume percent), 40 g of a solvent medium, and 30 g of an amino-based curing agent (coating film equivalent of 21%) were weighed and were agitated for two minutes in a planetary rotation device (AR-100; Thinky). As a result, the coating material for the organic layer 151 according to the first working example was obtained. As the epoxy resin, jER806 (Mitsubishi Chemical Corporation) was used. The epoxy resin and the silicate oligomer were so mixed that the volume ratio therebetween was 10:1. As the methyl silicate oligomer, MS51 (Mitsubishi Chemical Corporation) was used. As the solvent medium, 1-methoxy-2-propanol (Kishida Chemical Co. Ltd.) was used. As the curing agent, ADEKA HARDENER EH-6019 (ADEKA) was used.

Regarding the organic layer 152; 100 g of urethane acrylate, 3 g of a photo initiator, and 40 g of a solvent medium were weighed and were agitated for two minutes in a planetary rotation device (AR-100; Thinky). As a result, the coating material for the organic layer 152 according to the first working example was obtained. As the urethane acrylate, NOSTRA DBH (Mitsui Chemicals) was used. As the photo initiator, Omnirad 1173 (IGM Resins B. V.) was used. As the solvent medium, 1-methoxy-2-propanol (Kishida Chemical Co. Ltd.) was used.

<Preparation of Film>

In the first working example, the film was prepared in the following manner. Regarding the coating material, test pieces were prepared in the following manner for the purpose of using them in film hardness evaluation, hydrophilicity evaluation, water resistance evaluation, ultrasound image evaluation based on development or no development of air bubbles in a gel, and ultrasound image evaluation during inactivity of the ultrasound probe.

Firstly, spin coating was performed on the base material 150 in such a way that the organic layer 151 had the film thickness of 5 μm, and the base material 150 was cured by heating it at 120° C. for 60 minutes. Then, a film was formed on the organic layer 151 in such a way that the organic layer 152 had the film thickness of 4 μm, and the organic layer 152 was irradiated for 20 seconds in a UV curing device at 50 mW/cm2. As a result, the film according to the first working example was obtained. As the base material 150, polymethyl pentene (Mitsui Chemicals) was used.

Second Working Example to 12-Th Working Example

In the second working example to the 12-th working example, the coating material and the film were manufactured in an identical manner to the first working example, except that the materials and the conditions were varied as given below in Table 1 and Table 2.

In the second working example, ethyl silicate 48 (Colcoat Co. Ltd.) was used as ethyl silicate oligomer. In the third working example, EMS-485 (Colcoat Co. Ltd.) was used as the mixture of methyl silicate oligomer and ethyl silicate oligomer. In the fifth working example, 8UX-047A (Taisei Fine Chemical Co., Ltd.) was used as urethane acrylate. In the sixth working example, a mixture of 8UX-047A (Taisei Fine Chemical Co., Ltd.) and 8DK-3000 (Taisei Fine Chemical Co., Ltd.) in the weight percent of 1:1 was used as urethane acrylate. In the 12-th working example, a mixture of EPS-571 (DIC) and NOSTRA DBH (Mitsui Chemicals) in the weight percent of 1:1 was used as urethane acrylate.

TABLE 1

| | | | film in first working example | film in second working example | film in third working example | film in fourth working example | film in fifth working example | film in sixth working example |
|---|---|---|---|---|---|---|---|---|
| first organic layer | base resin | material | epoxy resin | epoxy resin | epoxy resin | epoxy resin | epoxy resin | epoxy resin |
| | | content ratio (volume %) | 71.4 | 66.7 | 72.5 | 64.5 | 71.4 | 71.4 |
| | silicate oligomer | material | methyl silicate oligomer | ethyl silicate oligomer | methyl silicate oligomer/ ethyl silicate oligomer | methyl silicate oligomer | methyl silicate oligomer | methyl silicate oligomer |
| | | content ratio (volume %) | 7.1 | 13.3 | 5.8 | 16.1 | 7.1 | 7.1 |
| | curing agent | material | amino-based curing agent | amino-based curing agent | amino-based curing agent | amino-based curing agent | amino-based curing agent | amino-based curing agent |
| | | content ratio (volume %) | 21 | 20 | 22 | 19 | 21 | 21 |
| | film thickness (μm) | | 5 | 5 | 5 | 5 | 5 | 5 |
| second organic layer | base resin | material | urethane acrylate | urethane acrylate | urethane acrylate | urethane acrylate | urethane acrylate | urethane acrylate |
| | | content ratio (volume %) | 97.0 | 97.1 | 97.1 | 97.1 | 97.1 | 97.1 |
| | curing agent | material | photo initiator | photo initiator | photo initiator | photo initiator | photo initiator | photo initiator |
| | | content ratio (volume %) | 3.0 | 2.9 | 2.9 | 2.9 | 2.9 | 2.9 |
| | film thickness (μm) | | 4 | 4 | 4 | 4 | 4 | 4 |
| characteristic of film | film hardness | | 3H or more | 3H or more | 3H or more | 3H or more | 2H | 1H |

TABLE 2

| | | | film in seventh working example | film in eighth working example | film in ninth working example | film in 10-th working example | film in 11-th working example | film in 12-th working example |
|---|---|---|---|---|---|---|---|---|
| first organic layer | base resin | material | epoxy resin | epoxy resin | epoxy resin | epoxy resin | epoxy resin | epoxy resin |
| | | content ratio (volume %) | 71.4 | 71.4 | 71.4 | 71.4 | 71.4 | 71.4 |
| | silicate oligomer | material | methyl silicate oligomer | ethyl silicate oligomer | methyl silicate oligomer | methyl silicate oligomer | methyl silicate oligomer | methyl silicate oligomer |
| | | content ratio (volume %) | 7.1 | 7.1 | 7.1 | 7.1 | 7.1 | 7.1 |
| | curing agent | material | amino-based curing agent | amino-based curing agent | amino-based curing agent | amino-based curing agent | amino-based curing agent | amino-based curing agent |
| | | content ratio (volume %) | 21.3 | 21.3 | 21.3 | 21.3 | 21.3 | 21.3 |
| | film thickness (μm) | | 15 | 3 | 17 | 5 | 5 | 5 |
| second organic layer | base resin | material | urethane acrylate | urethane acrylate | urethane acrylate | urethane acrylate | urethane acrylate | material having contact angle almost at 70° |
| | | content ratio (volume %) | 97 | 97 | 97 | 97 | 97 | 97 |
| | curing agent | material | photo initiator | photo initiator | photo initiator | photo initiator | photo initiator | photo initiator |
| | | content ratio (volume %) | 3 | 3 | 3 | 3 | 3 | 3 |
| | film thickness (μm) | | 4 | 4 | 4 | 3 | 15 | 4 |
| Characteristic of film | film hardness | | 3H or more | 3H or more | 3H or more | 3H or more | 3H or more | 3H or more |

(Evaluation Result)

Regarding the hydrophilicity, the water resistance, the black dot defects in ultrasound images, and the ultrasound image evaluation during inactivity of the ultrasound probe; the results of the first working example to the 12-th working example as obtained according to the methods explained above are given below in Table 3 and Table 4.

As long as the evaluation results fall within the ranges given below, it serves the purpose. Regarding the hydrophilicity, it serves the purpose as long as the water contact angle is smaller than 70°, and is more desirably smaller than 60°. Regarding the water resistance test, it serves the purpose as long as there is no change in the external appearance; and it is more desirable if there is no peeling off during the crosscut test performed after the water resistance test. Regarding the pencil hardness, it serves the purpose as long as the pencil hardness is equal to or greater than 2H, and is more desirably equal to or greater than 3H. Regarding the black dot defect amount in ultrasound images, it serves the purpose as long as the black dot defect amount is lower than 15%; it is better if the black dot defect amount is lower than 10%; and it is more desirable if the black dot defect amount is lower than 1%. Regarding the ultrasound images during inactivity of the ultrasound probe, it serves the purpose as long as the luminance ratio of ultrasound images is equal to or higher than 90%, and more desirably equal to or higher than 95%.

As illustrated in Table 3, the evaluation was performed for the film according to the first working example in which: the base material 150 contained polymethyl pentene; the organic layer 151 contained 71.4 volume percent of epoxy resin, 7.1 volume percent of silicate oligomer, and 21% of an amino-based curing agent; the organic layer 152 contained 97 volume percent of urethane acrylate and 3 volume percent of a photo initiator; and the film hardness was equal to or greater than 3H. As a result, the hydrophilicity was smaller than 60°, which was exceptionally good. Moreover, since there was no peeling off or no change in the external appearance during the crosscut test, the water resistance was exceptionally good. Furthermore, the black dot defect amount of ultrasound images was lower than 1%, which was exceptionally good. Moreover, the luminance ratio of ultrasound images during inactivity of the ultrasound probe was equal to or higher than 95%, which was exceptionally good.

With reference to Table 3, evaluation was also performed for the film according to the second working example in which adjustment was so performed that, as compared to the first working example, the content of ethyl silicate oligomer was higher at 13.3 volume percent and the volume ratio of epoxy resin and silicate oligomer was 10:2. As a result, the hydrophilicity was smaller than 60°, which was exceptionally good. Moreover, since there was no peeling off or no change in the external appearance during the crosscut test, the water resistance was exceptionally good. Furthermore, the black dot defect amount of ultrasound images was lower than 1%, which was exceptionally good. Moreover, the luminance ratio of ultrasound images during inactivity of the ultrasound probe was equal to or higher than 95%, which was exceptionally good.

With reference to Table 3, evaluation was also performed for the film according to the third working example in which adjustment was so performed that, as compared to the first working example, the content of ethyl silicate oligomer was lower at 5.8 volume percent and the volume ratio of epoxy resin and silicate oligomer was 10:0.8. As a result, the hydrophilicity was smaller than 60°, which was exceptionally good. Moreover, since there was some peeling off but no change in the external appearance during the crosscut test, the water resistance was good. Furthermore, the black dot defect amount of ultrasound images was lower than 1%, which was exceptionally good. Moreover, the luminance ratio of ultrasound images during inactivity of the ultrasound probe was equal to or higher than 90% but lower than 95%, which was good.

With reference to Table 3, evaluation was also performed for the film according to the fourth working example in which adjustment was so performed that, as compared to the first working example, the content of ethyl silicate oligomer was higher at 16.1 volume percent and the volume ratio of epoxy resin and silicate oligomer was 10:2.5. As a result, the hydrophilicity was smaller than 60°, which was exceptionally good. Moreover, since there was some peeling off but no change in the external appearance during the crosscut test, the water resistance was good. Furthermore, the black dot defect amount of ultrasound images was lower than 1%, which was exceptionally good. Moreover, the luminance ratio of ultrasound images during inactivity of the ultrasound probe was equal to or higher than 95%, which was exceptionally good.

With reference to Table 3, evaluation was also performed for the film according to the fifth working example in which, as compared to the first working example, the film hardness was adjusted to be lower at 2H. As a result, the hydrophilicity was smaller than 60°, which was exceptionally good. Moreover, since there was no peeling off or no change in the external appearance during the crosscut test, the water resistance was exceptionally good. Furthermore, the black dot defect amount of ultrasound images was lower than 1%, which was exceptionally good. Moreover, the luminance ratio of ultrasound images during inactivity of the ultrasound probe was equal to or higher than 95%, which was exceptionally good. However, due to a lower film hardness, the abrasion resistance was slightly lower, but was still within the satisfactory range.

With reference to Table 3, evaluation was also performed for the film according to the sixth working example in which, as compared to the first working example, the film hardness was adjusted to be lower at 1H. As a result, the hydrophilicity was smaller than 60°, which was exceptionally good. Moreover, since there was no peeling off or no change in the external appearance during the crosscut test, the water resistance was exceptionally good. Furthermore, the black dot defect amount of ultrasound images was lower than 1%, which was exceptionally good. Moreover, the luminance ratio of ultrasound images during inactivity of the ultrasound probe was equal to or higher than 95%, which was exceptionally good. However, due to a lower film hardness, the abrasion resistance was lower, but was still within the satisfactory range.

With reference to Table 4, evaluation was also performed for the film according to the seventh working example in which, as compared to the first working example, the film thickness of the organic layer 151 was adjusted to be higher at 15 μm. As a result, the hydrophilicity was smaller than 60°, which was exceptionally good. Moreover, since there was no peeling off or no change in the external appearance during the crosscut test, the water resistance was exceptionally good. Furthermore, the black dot defect amount of ultrasound images was lower than 1%, which was exceptionally good. Moreover, the luminance ratio of ultrasound images during inactivity of the ultrasound probe was equal to or higher than 90% but lower than 95%, which was good.

With reference to Table 4, evaluation was also performed for the film according to the eighth working example in which, as compared to the first working example, the film thickness of the organic layer 151 was adjusted to be lower at 3 μm. As a result, the hydrophilicity was smaller than 60°, which was exceptionally good. Moreover, since there was some peeling off but no change in the external appearance during the crosscut test, the water resistance was good. Furthermore, the black dot defect amount of ultrasound images was lower than 1%, which was exceptionally good. Moreover, the luminance ratio of ultrasound images during inactivity of the ultrasound probe was equal to or higher than 95%, which was exceptionally good.

With reference to Table 4, evaluation was also performed for the film according to the ninth working example in which, as compared to the first working example, the film thickness of the organic layer 152 was adjusted to be higher at 17 μm. As a result, the hydrophilicity was smaller than 60°, which was exceptionally good. Moreover, since there was no peeling off or no change in the external appearance during the crosscut test, the water resistance was exceptionally good. Furthermore, the black dot defect amount of ultrasound images was lower than 1%, which was exceptionally good. Moreover, the luminance ratio of ultrasound images during inactivity of the ultrasound probe was equal to or higher than 90% but lower than 95%, which was in the workable range.

With reference to Table 4, evaluation was also performed for the film according to the 10-th working example in which. as compared to the first working example, the film thickness of the organic layer 152 was adjusted to be lower at 3 μm. As a result, the hydrophilicity was smaller than 60°, which, as compared to the first working example, the film thickness of the organic layer 152 was adjusted to be lower at 15 μm. As a result, the hydrophilicity was smaller than 60°, which was exceptionally good. Moreover, since there was no peeling off or no change in the external appearance during the crosscut test, the water resistance was exceptionally good. Furthermore, the black dot defect amount of ultrasound images was lower than 1%, which was exceptionally good. Moreover, the luminance ratio of ultrasound images during inactivity of the ultrasound probe was equal to or higher than 90% but lower than 95%, which was within the satisfactory range.

With reference to Table 4, evaluation was also performed for the film according to the 12-th working example in which adjustment was so performed that, as compared to the first working example, urethane acrylate of the organic layer 152 was changed to a mixture of EPS-571 (DIC) and NOSTRA DBH (Mitsui Chemicals) in the weight percent of 1:1. As a result, the hydrophilicity was smaller than 70°, which was within the satisfactory range. Moreover, since there was no peeling off or no change in the external appearance during the crosscut test, the water resistance was exceptionally good. Furthermore, the black dot defect amount of ultrasound images was equal to or higher than 10% but lower than 15%, which was within the satisfactory range. Moreover, the luminance ratio of ultrasound images during inactivity of the ultrasound probe was equal to or higher than 95%, which was within the satisfactory range.

TABLE 3

|  | film in first working example | film in second working example | film in third working example | film in fourth working example | film in fifth working example | film in sixth working example |
|---|---|---|---|---|---|---|
| hydrophilicity | A | A | A | A | A | A |
| water resistance | A | A | B | B | A | A |
| black dot defect amount of ultrasound images | A | A | A | A | A | A |
| ultrasound images during inactivity of ultrasound probe | A | A | B | A | A | A |

TABLE 4

|  | film in seventh working example | film in eighth working example | film in ninth working example | film in 10-th working example | film in 11-th working example | film in 12-th working example |
|---|---|---|---|---|---|---|
| hydrophilicity | A | A | A | A | A | B |
| water resistance | A | B | A | A | A | A |
| black dot defect amount of ultrasound images | A | A | A | A | A | C |
| ultrasound images during inactivity of ultrasound probe | B | A | B | A | B | A | which was exceptionally good. Moreover, since there was no peeling off or no change in the external appearance during the crosscut test, the water resistance was exceptionally good. Furthermore, the black dot defect amount of ultrasound images was lower than 1%, which was exceptionally good. Moreover, the luminance ratio of ultrasound images during inactivity of the ultrasound probe was equal to or higher than 95%, which was exceptionally good. However, due to a lower film hardness, the abrasion resistance was slightly lower, but was still within the satisfactory range.

With reference to Table 4, evaluation was also performed for the film according to the 11-th working example in First Comparison Example to Third Comparison Example In an identical manner to the first working example to the 12-th working example explained above, test pieces were prepared for the purpose of using them for comparison regarding coating material adjustment, film adjustment, film hardness evaluation, hydrophilicity evaluation, water resistance evaluation, ultrasound image evaluation based on development or no development of air bubbles in a gel, and ultrasound image evaluation during inactivity of the ultrasound probe. Given below is the explanation of the differences with the first working example to the 12-th working example.

In Table 5 are illustrated the following details: the material constitution and the content of organic layers A and B that constitute the film according to a first comparison example to the third comparison example; and the characteristics of the film. In Table 6 are illustrated the results of evaluation performed using the film according to the first comparison example to a third comparison example. Herein, the organic layer A is formed at the position corresponding to the organic layer 151 according to the present embodiment, but has a different material constitution than the organic layer 151. Moreover, the organic layer B is formed at the position corresponding to the organic layer 152 according to the present embodiment, but has a different material constitution than the organic layer 152.

With reference to Table 6, evaluation was performed for the film according to the first comparison example in which adjustment was so performed that, as compared to the first working example, the organic layer A of the film does not contain silicate oligomer. Since silicate oligomer was not included, the film could not be formed in a uniform manner. In that case, the hydrophilicity was smaller than 60°, which was exceptionally good. However, during the crosscut test, there was peeling off as well as a change in the external appearance. Hence, the water resistance was not good. The black dot defect amount of ultrasound images was lower than 1%, which was exceptionally good. However, the luminance ratio of ultrasound images during inactivity of the ultrasound probe was lower than 90%, which was not good.

With reference to Table 6, evaluation was performed for the film according to the second comparison example in which adjustment was so performed that, as compared to the first working example, olefin resin was used as the base resin in the organic layer A. As a result, the hydrophilicity was smaller than 60°, which was exceptionally good. However, during the crosscut test, there was peeling off as well as a change in the external appearance. Hence, the water resistance was not good. The black dot defect amount of ultrasound images was lower than 1%, which was exceptionally good. Moreover, the luminance ratio of ultrasound images during inactivity of the ultrasound probe was equal to or higher than 95%, which was exceptionally good.

With reference to Table 6, evaluation was performed for the film according to the third comparison example in which adjustment was so performed that, as compared to the first working example, epoxy resin was used as the base resin in the organic layer B. As a result, the hydrophilicity was equal to or greater than 70°, which was not good. On the other hand, since there was no peeling off or no change in the external appearance during the crosscut test, the water resistance was exceptionally good. However, the black dot defect amount of ultrasound images was equal to or higher than 15%, which was not good. On the other hand, the luminance ratio of ultrasound images during inactivity of the ultrasound probe was equal to or higher than 95%, which was exceptionally good.

TABLE 5

|  |  |  | film in first comparison example | film in second comparison example | film in third comparison example |
| --- | --- | --- | --- | --- | --- |
| first organic layer | base resin | material | epoxy resin | olefin resin | epoxy resin |
|  |  | content ratio (volume %) | 76.9 | 71.4 | 71.4 |
|  | silicate oligomer | material | none | methyl silicate oligomer | methyl silicate oligomer |
|  |  | content ratio (volume %) | 0.0 | 7.1 | 7.1 |
|  | curing agent | material | amino-based curing agent | amino-based curing agent | amino-based curing agent |
|  |  | content ratio (volume %) | 23 | 21.3 | 21.3 |
|  | film thickness (μm) |  | 5 | 5 | 5 |
| second organic layer | base resin | material | urethane acrylate | urethane acrylate | epoxy resin |
|  |  | content ratio (volume %) | 97.1 | 97 | 97 |
|  | curing agent | material | photo initiator | photo initiator | photo initiator |
|  |  | content ratio (volume %) | 2.9 | 3 | 3 |
|  | film thickness (μm) |  | 4 | 4 | 4 |
| characteristic of film | film hardness |  | 3H or more | 3H or more | 3H or more |

TABLE 6

|  | film in first comparison example | film in second comparison example | film in third comparison example |
| --- | --- | --- | --- |
| hydrophilicity | A | A | C |
| water resistance | D | D | A |
| black dot defect amount of ultrasound images | A | A | C |
| ultrasound images during inactivity of ultrasound probe | C | A | A |

According to at least one embodiment described above, it becomes possible to reduce the attenuation coefficient in the acoustic lens as well as to enhance hydrophilicity and resistance therein.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound probe comprising:
a base material configured to contain polyolefin;
a first organic layer configured to be formed on outer surface of the base material and to contain epoxy resin and silicate oligomer; and
a second organic layer configured to be formed on outer surface of the first organic layer and to have hydrophilicity.

2. The ultrasound probe according to claim 1, wherein the first organic layer contains, as the silicate oligomer, at least either methyl silicate oligomer or ethyl silicate oligomer.

3. The ultrasound probe according to claim 1, wherein the second organic layer has film hardness equal to or greater than 3H in terms of pencil hardness.

4. The ultrasound probe according to claim 1, wherein, in the first organic layer, content ratio of the epoxy resin and the silicate oligomer is in range of 10:0.1 volume percent to 10:5 volume percent.

5. The ultrasound probe according to claim 1, wherein, in the first organic layer, content ratio of the epoxy resin and the silicate oligomer is in range of 10:1 volume percent to 10:2 volume percent.

6. The ultrasound probe according to claim 1, wherein the first organic layer contains silicon oxide as a result of hydrolysis of the silicate oligomer.

7. An acoustic lens comprising:
a base material configured to contain olefin;
a first organic layer configured to be formed on outer surface of the base material and to contain epoxy resin and silicate oligomer; and
a second organic layer configured to be formed on outer surface of the first organic layer and to have hydrophilicity.

8. An ultrasound diagnosis apparatus comprising an ultrasound probe that includes
a base material configured to contain olefin,
a first organic layer configured to be formed on outer surface of the base material and to contain epoxy resin and silicate oligomer, and
a second organic layer configured to be formed on outer surface of the first organic layer and to have hydrophilicity.

9. A coupler for ultrasound probes, comprising:
a base material configured to contain olefin;
a first organic layer configured to be formed on outer surface of the base material and to contain epoxy resin and silicate oligomer; and
a second organic layer configured to be formed on outer surface of the first organic layer and to have hydrophilicity.

* * * * *